Figure 1:
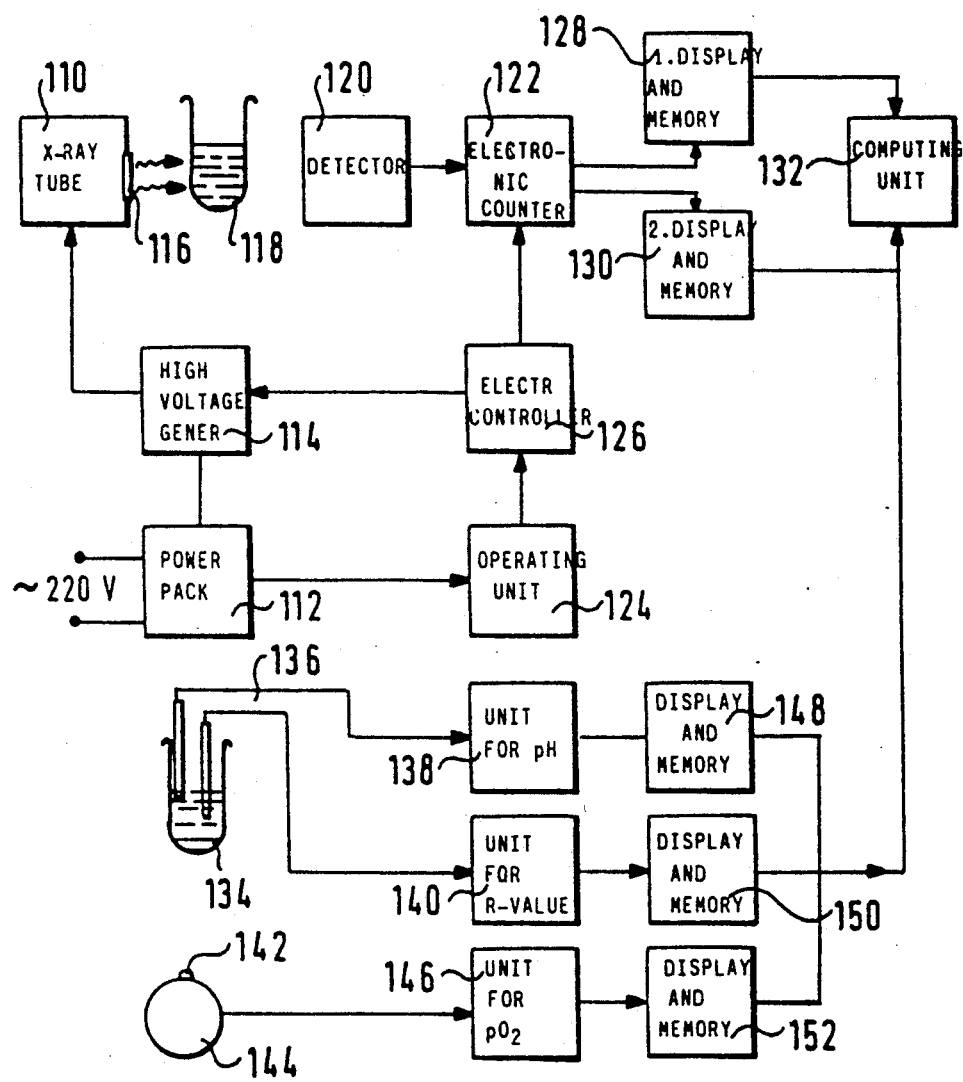

United States Patent [19]
Wolf

[11] Patent Number: 5,157,703
[45] Date of Patent: Oct. 20, 1992

[54] METHOD AND DEVICE FOR THE EXAMINATION OF CELLULAR CHANGES IN AN ORGANISM

[76] Inventor: Hans-Detlef Wolf, Bühlstrasse 68, D-7742 St. Georgen, Fed. Rep. of Germany

[21] Appl. No.: 700,357
[22] PCT Filed: Jun. 18, 1988
[86] PCT No.: PCT/DE88/00367
   § 371 Date: Feb. 21, 1989
   § 102(e) Date: Feb. 21, 1989
[87] PCT Pub. No.: WO88/10094
   PCT Pub. Date: Dec. 29, 1988

Related U.S. Application Data

[63] Continuation of Ser. No. 334,110, Feb. 21, 1989, abandoned.

[30] Foreign Application Priority Data

Oct. 1, 1981 [DE] Fed. Rep. of Germany ....... 3733267
Jun. 24, 1987 [DE] Fed. Rep. of Germany ....... 3720827

[51] Int. Cl.$^5$ .............................................. H05G 1/64
[52] U.S. Cl. ......................................... 378/99; 358/111
[58] Field of Search ........................... 378/99; 358/111

[56] References Cited

U.S. PATENT DOCUMENTS 3,848,130 11/1974 Macovski .
3,854,049 12/1974 Mistretta et al. .
4,399,457 8/1983 Riederer et al. ...................... 378/99

OTHER PUBLICATIONS

Baily et al., Medical Physics, vol. 3, No. 3, May/Jun. 1976, pp. 176-180, Tumor Localization and Beam Monitoring—Electrofluorotomography.
Battista et al., Phys. Med. Biol., 1981, vol. 26, No. 1, pp. 81-99, Compton Scatter Imaging of Transverse Sections: An Overall Appraisal and Evaluation for Radiotherapy Planning.
Gustafsson et al., Med. and Biol. Engineering, Jan. 1974, pp. 113-119, vol. 12, No. 1, X-Ray Spectrophotometry for Bone-Mineral Determinations.

Primary Examiner—Craig E. Church
Attorney, Agent, or Firm—Donald Brown

[57] ABSTRACT

To investigate cellular changes in a living organism, in particular pathological cellular changes in a human being, the cellular substance is irradiated with two x-ray pulses in rapid succession. The difference in attenuation of the intensity between the two x-ray pulses is then evaluated.

2 Claims, 2 Drawing Sheets

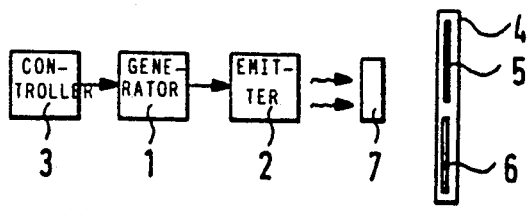
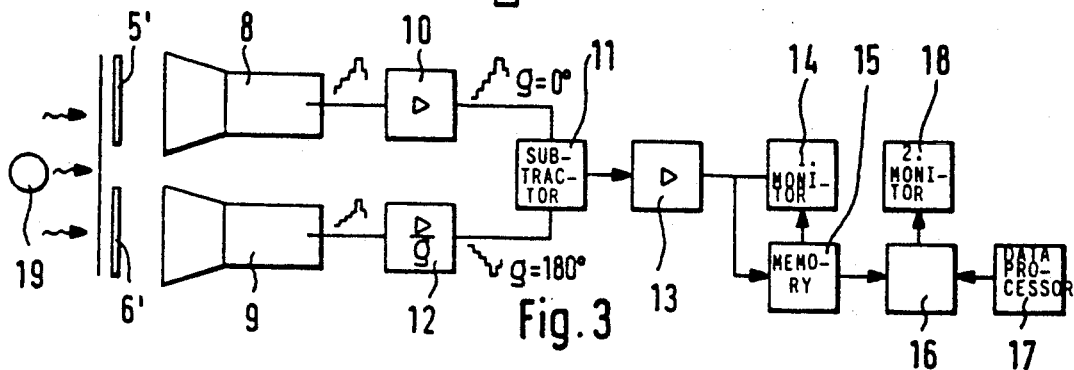
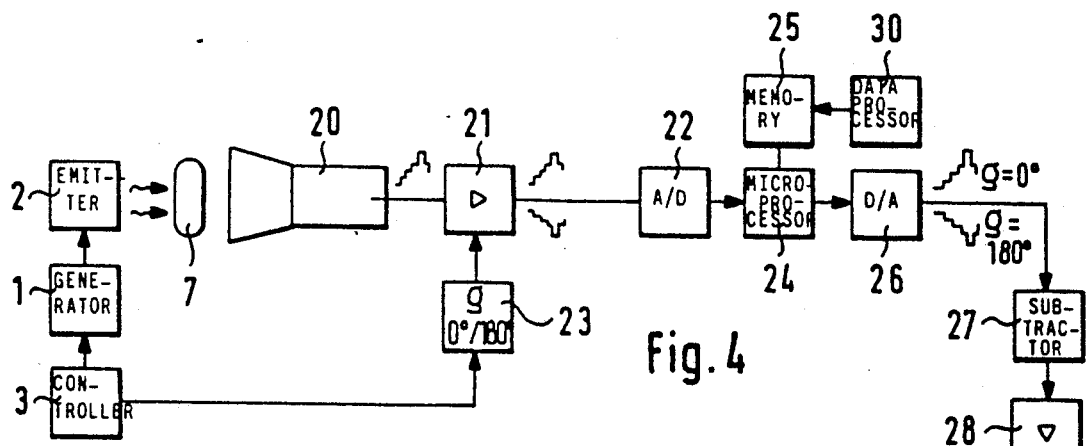
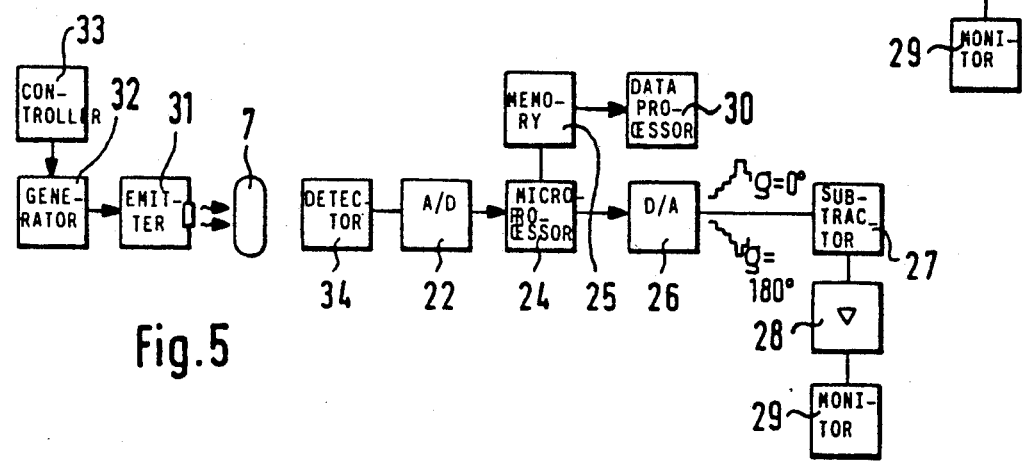

METHOD AND DEVICE FOR THE EXAMINATION OF CELLULAR CHANGES IN AN ORGANISM

This is a continuation of copending application Ser. No. 07/334,110 filed on Feb. 21, 1989 now abandoned.

The invention relates to a method of examining cellular changes in an organism, specifically pathological cellular changes in a human being, and to a device for carrying through this method.

The examination and study of the cell structure is of emient importance in research and particularly in medicine. It involves the early detection of pathological cellular changes such as those occurring with cancer, which is frequently of vital importance for an appropriate therapy. It has been common so far to determine such cellular changes under the microscope. This method is comparatively expensive since, on the one hand, it requires the excision of tissue and, on the other hand, the preparation and staining of the microscopic section is time-consuming.

Organ-imaging methods so far common such as conventional X-ray methods, computer tomographic or nuclear-spin resonance methods entail the disadvantage of being comparatively complicated to apply and of being hardly suitable for screening applications. As a result, cancerous tissue is detected either too late or not unambiguously.

The invention is based on the object of providing a method and a device by means of which an early detection of cellular changes in an organism will be possible with a low expenditure in work and time.

Expedient embodiments of the invention are defined in the subclaims made dependent on the foregoing claims.

The invention is based on the finding that the interaction of X-radiation with the cellular substance is influenced by an immediately preceding exposure to X-rays. In accordance with the invention, the cellular substance to be examined is accordingly irradiated with two X-ray pulses in immediate succession. In this method, the respective interaction between the X-radiation and the cellular substance is determined by measuring or recording the intensity of the transmitted X-rays or the weakening of the intensity of the X-radiation, respectively. The first X-ray pulse results in an excitation of the cellular substance so that the second X-ray pulse will be transmitted through the excited cellular substance. It has become evident that the first X-radiation pulse will undergo a stronger weakening by the cellular substance than does the immediately following second X-radiation pulse. When two X-radiation pulses of the same spectral intensity distribution will be emitted through the same cellular substance in immediate succession a transmitted intensity will be measured for the second X-radiation pulse which is higher than the intensity measured for the first X-radiation pulse.

Moreover, the invention utilizes the finding that the difference of the weakening of the X-radiation intensity between the first and the second X-radiation pulse depends on the condition of the cells in the irradiated substance. In accordance with the invention, the condition of the cells in the substance may therefore be concluded from the measured difference in the weakening of the first and the second X-radiation pulse. In particular with pathological cellular changes a distinctly measurable change of the difference in weakening will occur in a comparison against healthy cells.

It is a known fact that healthy cells of organisms present a bioelectric potential in the range between 50 and 100 mV approximately, and between some 90 and 100 mV in man. According to more recent studies, this bioelectric potential of the cell breaks down to roughly 30 to 10 mV approximately in the event of cancer. It is assumed that this depolarization of the cell, which occurs in the event of carcinomatous involvement, is also linked up with the change of the cellular structure which results in the change of the difference in weakening which the invention makes use of to detect the change in the cell.

In an embodiment of the invention, a sample containing the cellular material to be examined is exposed to X-radiation pulses of the same spectral intensity distribution and the same overall intensity in immediate succession. The transmitted intensity of the X-radiation is detected, using a detector behind the sample, as a measure of the interaction between the X-radiation and the cellular substance. The difference in intensity is determined between the second and the first X-radiation pulse, and is compared against a standard corresponding to a healthy cellular material.

Any sample containing cellular substance may be used as sample material. It may be a tissue sample of the organism. A blood sample is preferably used since it is easy to take. As the aforementioned depolarization of the cells occurs all through the bloodstream in the event of carcinomatous involvement the examination of a blood sample will furnish information about carcinomatous involvement at any location in the body. The inventive method is therefore suited specifically for simple early diagnosis of cancer.

In the practical implementation of the inventive method the use of an X-radiation has proven to be expedient which presents a substantially continuous energy spectrum, such as a radiation as emitted by an X-ray tube. The upper threshold energy of the X-ray spectrum is expediently in the range of some 30 keV. X-radiation of higher energy will present a reduced interaction and moreover involves higher engineering demands on the device generating the X-radiation.

The time interval between the two X-radiation pulses should be less than 1 sec. approximately. With a longer interval the difference in X-radiation weakening will become too small. A 100 $\mu$sec time interval between the two X-radiation pulses has turned out to be most expedient. With this time interval a well-measurable difference in the X-radiation weakening is achieved while this time interval can be well managed in terms of X-radiation source control as well as detector control.

Any detector known per se may be used for detection, which is endowed with a sufficiently sensitive response characteristic covering the entire energy spectrum of X-radiation. Preferably, a Geiger-Mueller counter or a scintillation counter is used. These detectors record the transmitted X-radiation intensity in the form of a digital pulse-counting rate which is easy to process electronically. In particular the weakening of the X-radiation of the first and the second radiation pulse may be easily detected in the form of a difference in the pulse-counting rate. The intensity may also be measured by detection of the transmission density of an X-ray film plate.

The difference in the X-ray attenuation between the first and the second X-radiation pulse is not only influenced by the properties of the cell but depends, of course, also on other physico-chemical parameters of the sample. A diagnosis established on the basis of a comparison of the measured value against the standard therefore requires that the measured value and the standard be referred to the same conditions in terms of these additional parameters. To ensure this in a manner which is simple and expedient for practical application the essential sample parameters are measured in a manner known per se and considered in computing for adjustment of the standard or the measured value, in addition to the X-radiation measurement. The essential parameters which will thus be considered in a blood specimen are the pH value (hydrogen ion concentration), the $pO_2$ value (oxygen concentration) and the r-value (electric conductance).

As the different weakening of the X-radiation intensity in the first and in the second X-radiation pulse involves a differential measurement it is also required, of course, to establish also the absolute intensity of the X-radiation, e.g. by way of a calibration measurement without sample, and to consider this value in the analytical evaluation by computation.

In another embodiment of the invention, the cellular change may be examined even without taking a tissue sample. That part of the body which contains the tissue to be examined is irradiated with the two X-radiation pulses at the small time interval. In this method the transmitted radiation intensity of each of the two X-radiation pulses is recorded so that an X-ray image of the region containing the tissue to be examined will be obtained. In a differential method, the intensity distributions of the respective recordings of the two X-radiation pulses are subtracted from each other spot by spot within a scanning grid. What results from this subtraction is the distribution of the difference in intensity, with the tissue area affected by a pathological cellular change, e.g. an area showing carcinomatous involvement, distinctly contrasting from the surrounding tissue including a healthy cell structure.

Engineering means known per se may be employed to record the intensity distribution of both X-radiation pulses and to generate the difference of the two recordings.

In the following embodiments of the invention will be described in more detail with reference to the attached drawing wherein:

FIG. 1 shows the basic structure of a device for examination of a sample of a cellular substance, FIG. 2 illustrates an X-ray device generating recordings for the differential evaluation, FIG. 3 shows a device for evaluation of the recordings generated by means of the device shown in FIG. 2, FIG. 4 represents a modified device generating recordings and evaluating the recordings, and FIG. 5 illustrates another embodiment of a recording device including evaluation means.

In the embodiment of FIG. 1 an X-ray tube 110 is operated by means of a power pack 112 and a high-voltage generator 114 at a voltage of roughly 30 kV. The radiation emitted from the X-ray tube through a filter 116 is transmitted through a blood sample contained in an appropriate sample receptacle 118 such as a narrow test flume of 3 ml capacity approximately. The X-radiation transmitted through the blood sample hits a detector 120 such as a Geiger-Mueller counter operating on the triggering or excitation principle. The pulses determined by the detector 120 are counted in an electronic counter 122. An electronic controller 126 is activated via an operating unit 124. The electronic controller 26 controls the operation of the X-ray tube 110 such that the latter will emit two identical radiation pulses at a time interval of roughly 100 msec. At the same time, the electronic controller 126 controls the output of the electronic counter 122 in a way that the pulse-counting rate corresponding to the first X-radiation pulse will be supplied to a first display and memory unit 128 while the pulse-counting rate corresponding to the second X-radiation pulse will be fed to a second display and memory unit 130. The pulse-counting rates of the first and the second X-radiation pulses, which are stored in the display and memory units 128 and 130, are applied to a computing unit 132 for analytical evaluation.

In another sample 134 of the blood specimen to be examined, the pH value is conventionally measured by means of electrodes 136 in a unit 138 whereas the electric conductance (r-value) is measured in a unit 140. Eventually, one drop 142 of the blood to be examined is applied, in a manner known per se, onto a $pO_2$ sensor 144 for measurement of the $pO_2$ value in a conventinal unit 146. The values measured in the units 138, 140 and 146 are stored in associated display and memory units 148, 150 and 152 and supplied to the computing unit 132.

In the computing unit 132 the difference between the pulse-counting rates of the second X-radiation pulse and the first X-radiation pulse is computed as the measured value. This measured value is adjusted by computation, employing the pulse-counting rate measured without the sample 118. The adjusted value of measurement is then compared in the computing unit 132 against a standard established from a sample 118 of the blood of a healthy individual. In the computing unit 132, the values determined by the units 138, 140 and 146 are used to consider the variations of these physico-chemical parameters of the sample under examination in relation to the sample used to measure the standard.

In another embodiment, a device illustrated in FIG. 2 comprises a conventional X-ray apparatus including a generator 1, an emitter 2 and an electric controller 3 for the generator. A cartridge 4 accomodating an X-ray film 5 for a first image and an X-ray film 6 for a second image is provided as the receiver. The object 7 to be examined is placed between the emitter 2 and the cartridge 4 containing the X-ray films. The controller 3 is so designed that two X-ray film shots can be made on the first and the second X-ray film 5, 6 of the same organ to be examined with the same positioning, in succession at a short time interval, operating on conventional X-ray technology. The time difference is in the range of seconds and is preferably one to three seconds or even less than one second. Since the cellular molecules of the tissue to be examined are excited during the first X-ray film shot the X-radiation is attenuated or weakened during the second shot to a degree smaller than in the first shot. Thus a difference in the gray tints of the optical information on the two images on the X-ray films 5, 6 is created.

The images so created on the two X-ray films 5, 6 are evaluated by means of the device illustrated in FIG. 3. This device includes two video cameras 8, 9. The output side of the first camera 8 is connected to an amplifier 10 which in its turn is connected, via its output, to a subtractor unit 11. The output of the second video camera 9 is connected to an amplifier 12 which simultaneously provides for a phase reversal or paraphase amplification; its output is connected to the subtractor element 11. The output of the subtractor element 11 is connected via an amplifier 13 directly to a first monitor 14 and moreover to a video information memory 15. The output of the video information memory is connected, on the one hand, to the monitor 14 and, on the other hand, to a microcomputer. The microcomputer is linked up with an electronic data processor 17 and moreover with a second monitor 18. The X-ray films 5', 6' to be evaluated are disposed at a defined spacing from the video cameras. On that side of the X-ray films which is opposite to the side facing the video cameras a schematically outlined light source 19 is arranged to illuminate the films for evaluation.

The two X-ray films 5', 6' are scanned in registry by the video cameras 8, 9. The video signals so generated are electronically processed in a way that a positive and a negative video signal with corresponding amplitudes will be obtained. The signals supplied to the subtractor element 11 are subtracted there. The differential signal present at the output side is amplified in the amplifier 13 and displayed on the first monitor 14. With this arrangement, a video information will be displayed on the monitor only when the difference between the two video signals is different from zero. This will be the case only when the corresponding video information on both films 5', 6' is due to a cancerous tissue. The reason of this phenomenon is to be found in the different excitation energy of X-radiation with healthy tissue relative to cancerous tissue. The subtractor element is so set that amplitudes produced by healthy tissue will cancel each other and are thus not displayed on the monitor. The monitor thus displays only tissue which is affected. With the illustrated device it is possible to distinguish cancerous tissue easily and unambiguously from healthy tissue. The illustrated device is suited to buffer the created image electronically in the video memory 15 and to evaluate the information electronically by means of the microcomputer.

The device shown in FIG. 4 is distinguished from the device described in FIGS. 2 and 3 by the fact that provisions are made for electronic video information storage rather than for use of the X-ray films 5, 6. Like in case of FIG. 2, the device comprises a generator 1, an emitter 2, and a controller 3. A camera 20 which is sensitive to X-radiation is provided as receiver for the video information. The object 7 to be examined is disposed between the camera and the emitter 2.

The output side of the camera is connected to an amplifier 21 whose output, in its turn, is connected to an analog/digital converter 22. The electronic controller 3 is additionally linked up with a paraphase amplifier unit 23 whose output supplies the amplifier 21. The output side of the analog/digital converter 22 is connected to a microcomputer 24 which, in its turn, it connected via its output not only to a video information memory 25 but also to a digital/analog converter 26. The output of the digital/analog converter 26, in its turn, supplies a subtractor element 27 whose output is connected to an amplifier 28 with a monitor 29. The memory 25 is additionally linked up with an electronic data processor 30.

In operation, initially an image is created by the first exposure. The output signal from the camera 20 is suitably converted and buffered in the memory 25. Then a second image is created by the second irradiation step which follows at a short time interval. The paraphase amplifier 23 is used to reverse the phase of the amplitude signal obtained therefrom. The thus generated signal is subtracted from the buffered video information in a manner comparable to that applying to the aforedescribed embodiment, so that, as with the aforedescribed embodiment, only those parts will be displayed on the monitor 29 which originate from an affected tissue, specifically a cancerous tissue.

The device illustrated in FIG. 5 is distinguished from the aforedescribed device by the fact that the image is created on the principle of computer tomography rather than conventional X-radiation exposure. The device comprises a suitable emitter 31, a generator 32 and an electronic controller 33 to irradiate the object 7 to be examined in the manner common with computer tomography. On the opposite side a detector 34 is provided. The output side of that detector is connected to an analog/digital converter 35 with the adjoining elements 22 to 30 as in FIG. 4.

The electronic controller 33 is so designed that it repeats each pulse usual in computer tomography at the aforedescribed short interval. Thus, on the one hand, all pulses occurring with the conventional computer tomography are present at the most different angles. Additionally, all pulses are emitted a second time at the aforedescribed time interval. The detector 34 and the associated evaluation unit are so designed that a first image will be stored which is generated from the respective first pulses. Moreover, a second image is stored which originates from the respective second pulses. These two images are evaluated in the aforedescribed manner.

I claim:

1. An in vitro method of determining if a specimen of solid tissue or blood is healthy, which comprises the steps of applying a first x-ray pulse to said specimen and recording the strength of said x-ray pulse passing through said specimen and in less than one second after said first pulse is applied, applying a second x-ray pulse to said specimen and recording the strength of said x-ray pulse passing through said specimen, determining the difference in the strength of said first and second x-ray pulses passing through said specimen and then comparing said difference against the difference derived from a standardized healthy specimen of solid tissue or blood to determine of the specimen is healthy, including the step of calibrating the comparing for differences in physio-chemical properties of the healthy specimen and the physio-chemical properties of the specimen being examined in making the determination if the specimen being examined is healthy.

2. An in vitro method of determining if a specimen of blood is healthy, which comprises the steps of applying a first x-ray pulse to said specimen and recording the strength of said x-ray pulse passing through said specimen and in less than one second after said first pulse is applied, applying a second x-ray pulse to said specimen and recording the strength of said x-ray pulse passing through said specimen, determining the difference in the strength of said first and second x-ray pulses passing through said specimen and then comparing said difference against the difference derived from a standardized healthy specimen of solid tissue or blood to determine if the specimen is healthy, including the step of calibrating the comparing for the pH value, $PO_2$ value and r-value properties of the healthy specimen to the same properties of the specimen being examined in determining if the specimen being examined is healthy.

* * * * *